(12) United States Patent
Ferko et al.

(10) Patent No.: US 10,588,696 B2
(45) Date of Patent: Mar. 17, 2020

(54) PATELLA IMPLANT PLANNING

(71) Applicant: Mako Surgical Corp., Fort Lauderdale, FL (US)

(72) Inventors: Michael C. Ferko, Warwick, NY (US); Emily Hampp, Far Hills, NJ (US)

(73) Assignee: Mako Surgical Corp., Fort Lauderdale, FL (US)

( * ) Notice: Subject to any disclaimer, the term of this patent is extended or adjusted under 35 U.S.C. 154(b) by 117 days.

(21) Appl. No.: 15/227,433

(22) Filed: Aug. 3, 2016

(65) Prior Publication Data
US 2018/0036083 A1 Feb. 8, 2018

(51) Int. Cl.
| | | |
|---|---|---|
| *A61B 34/10* | (2016.01) | |
| *A61B 17/17* | (2006.01) | |
| *A61B 17/56* | (2006.01) | |
| *A61F 2/46* | (2006.01) | |
| *G16H 50/50* | (2018.01) | |

(52) U.S. Cl.
CPC .......... *A61B 34/10* (2016.02); *A61B 17/1767* (2013.01); *A61B 17/56* (2013.01); *A61F 2/46* (2013.01); *G16H 50/50* (2018.01); *A61B 2017/564* (2013.01); *A61B 2017/568* (2013.01); *A61B 2034/104* (2016.02); *A61B 2034/108* (2016.02); *A61F 2002/4633* (2013.01)

(58) Field of Classification Search
CPC ..... A61B 17/1767; A61B 17/56; A61B 34/10; A61F 2/46
See application file for complete search history.

(56) References Cited

U.S. PATENT DOCUMENTS

| | | |
|---|---|---|
| 4,896,661 A | 1/1990 | Bogert et al. |
| 5,122,130 A | 6/1992 | Keller |
| 6,261,296 B1 | 7/2001 | Aebi et al. |
| 6,712,825 B2 | 3/2004 | Aebi et al. |
| 6,856,828 B2 | 2/2005 | Cossette et al. |
| 7,377,924 B2 | 5/2008 | Raistrick et al. |
| 7,618,421 B2 | 11/2009 | Axelson, Jr. et al. |
| 8,571,637 B2 | 10/2013 | Sheffer et al. |

(Continued)

FOREIGN PATENT DOCUMENTS

| | | |
|---|---|---|
| EP | 1574171 A1 | 9/2005 |
| WO | 2015160852 A1 | 10/2015 |

OTHER PUBLICATIONS

Anglin, C. et al., "Biomechanical Consequences of Patellar Component Medialization in Total Knee Arthoplasty", The Journal of Arthoplasty, vol. 25, No. 5, Aug. 2010, pp. 793-802.

(Continued)

*Primary Examiner* — Christine A Enad
(74) *Attorney, Agent, or Firm* — Lerner, David, Littenberg, Krumholz & Mentlik, LLP

(57) ABSTRACT

Disclosed herein are systems and methods of patella preparation. A method of patella preparation includes creating a patellar coordinate system utilizing key honey landmarks of a patella on a virtual model of an unresected patella. The method can further include defining a resection plane at a predetermined implant thickness and aligning the resection plane with the patellar coordinate system. Implant selection can be finalized on the resection plane to meet predetermined tolerances. A navigated patella clamp with a tracker and stylus can then be used to intraoperatively resect the patella and locate the implant.

20 Claims, 9 Drawing Sheets

(56) References Cited

U.S. PATENT DOCUMENTS

| | | |
|---|---|---|
| 2002/0068942 A1 | 6/2002 | Neubauer et al. |
| 2003/0093217 A1 | 5/2003 | Petzold et al. |
| 2006/0052792 A1 | 3/2006 | Boettiger et al. |
| 2008/0154262 A1 | 6/2008 | Brundobler et al. |
| 2009/0043556 A1* | 2/2009 | Axelson ................ A61B 19/50 703/11 |
| 2009/0062869 A1 | 3/2009 | Claverie et al. |
| 2009/0157083 A1* | 6/2009 | Park ..................... A61B 5/055 606/88 |
| 2009/0183740 A1 | 7/2009 | Sheffer et al. |
| 2010/0177948 A1* | 7/2010 | Le Bras ............... A61B 5/1075 382/132 |
| 2011/0144760 A1* | 6/2011 | Wong ................. A61F 2/30942 623/20.14 |
| 2012/0209393 A1* | 8/2012 | Ries .................... A61F 2/3877 623/20.19 |
| 2013/0165939 A1 | 6/2013 | Ries et al. |
| 2014/0148909 A1 | 5/2014 | Angibaud |
| 2014/0244220 A1* | 8/2014 | McKinnon ............. A61F 2/02 703/1 |
| 2016/0100907 A1* | 4/2016 | Gomes ................. A61B 34/10 703/1 |
| 2016/0270859 A1* | 9/2016 | Park ..................... A61B 34/10 |
| 2017/0281202 A1 | 10/2017 | Hampp et al. |

OTHER PUBLICATIONS

Extended European Search Report for EP17184592 dated Mar. 14, 2018.

* cited by examiner

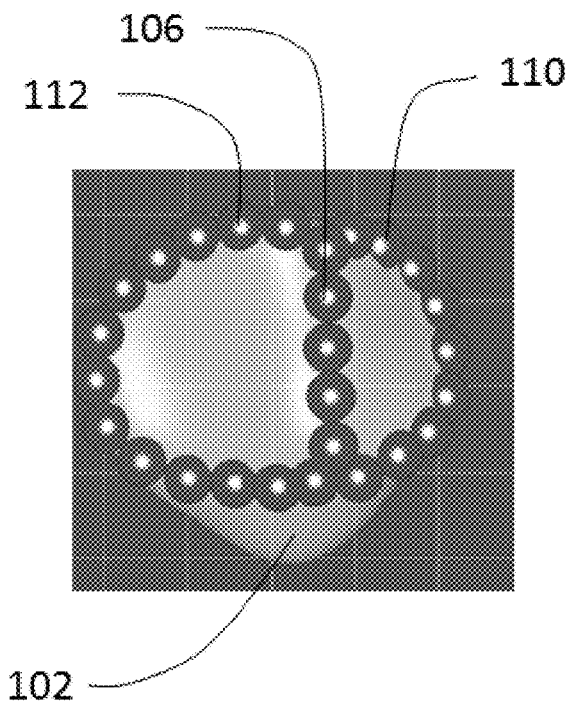 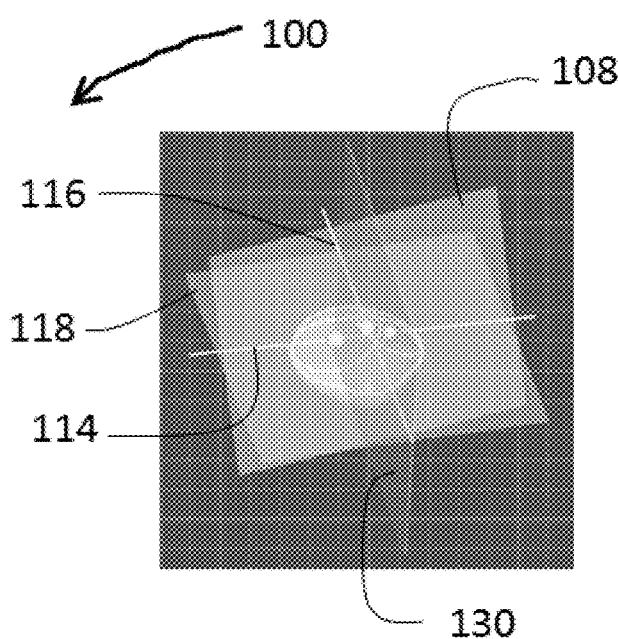
FIG. 6A  FIG. 6B
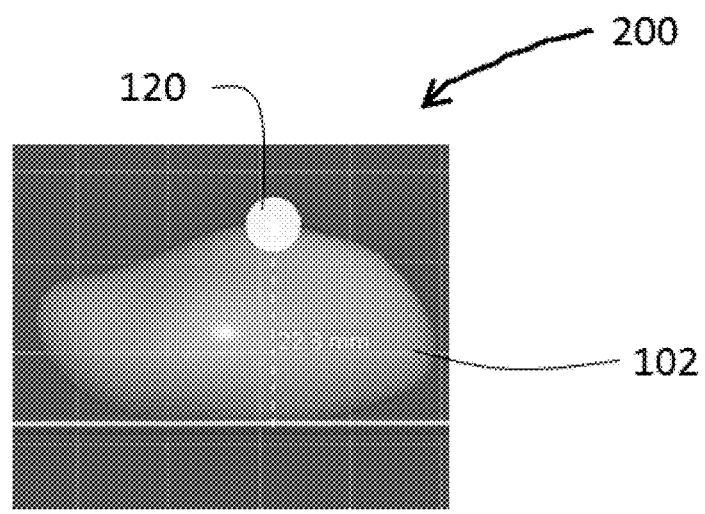
FIG. 7

PREOPERATIVE PLANNING 100
200 → Determining Patella Resection Plane 300
400 → Implant Selection and Placement Location

INTRAOPERATIVE PREPARATION

500 → Implant Placement using Patella Holder and Tracking Instrument Holder

FIG. 11

PATELLA IMPLANT PLANNING

FIELD OF THE INVENTION

The present invention relates to systems and methods to aid patella preparation and in particular relates to defining a resection plane aligned to a patella coordinate system and positioning a properly sized implant thereon.

BACKGROUND OF THE INVENTION

Total knee arthroplasty ("TKA") is generally performed to replace worn out knee joints with implants. Knee joints, including the patella, wear out over time or may be damaged by ailments such as arthritis. Proper sizing and placement of an implant to replace a damaged patella is crucial in ensuring a successful TKA. Improper implant sizing or poor positioning of the implant may lead to patellar maltracking causing anterior knee pain, increased implant wear, and consequently a higher risk of implant instability leading to patellar fracture. Therefore, ensuring that the natural kinematics of the patella are maintained after the TKA is desired for a successful surgery.

Selecting an implant with the correct thickness is necessary for a successful TKA. Insufficient resection thickness will increase the total height of the patella (with an implant) that will alter the biomechanics of the quadriceps and limit flexion. Whereas, excessive resection may result in a weak resected patella that is prone to patellar fracture. Resection thickness is generally determined based on the total thickness of the patella, which is measured using calipers. However, the irregular morphology of the patella makes it difficult to obtain accurate measurements from a caliper because of the lack of reference points on the patella.

While computer-assisted surgery ("CAS") procedures are available to assist in determining patella resections, there exists a need to provide a method to generate a patellar coordinate system to properly identify a resection plane and position a properly sized implant thereon.

BRIEF SUMMARY OF THE INVENTION

Disclosed herein are systems and methods for patella preparation. A preoperative plan may be developed to define a resection plane and size an implant such that the patella may be intraoperatively prepared and implanted with the selected implant.

Patella preparation generally requires three key steps: (1) determining a resection plane that is properly aligned with the natural patellar coordinates; (2) calculating the proper thickness of the resection plane, i.e., the thickness of the implant; and (3) proper placement of the implant on the resection plane. Aligning a resection plane to coincide with the patellar coordinate system will ensure that the natural kinematics of the patella is preserved after the TKA. However, the unique morphology of the patella makes it difficult to properly identify this patellar coordinate system.

A first aspect of the present invention is a method to generate a patellar coordinate system utilizing key honey landmarks of the patella. The honey landmarks are unique to each patella and allow for the identification of the natural coordinates of the patella. An unresected patella displayed on a graphical user interface is used to select key honey landmarks, and generate coordinate planes therefrom. This patellar coordinate system provides the natural coordinates of the patella and ensures that the natural kinematics of the patella is preserved after the surgery.

One embodiment of this first aspect is a method of generating an anatomical coordinate system for a virtual bone model of an irregularly shaped bone comprising selecting a first set of points along a vertical ridge of the virtual bone model defining a vertical ridge line; creating a reference plane transverse to the vertical ridge line; selecting a second set of points about a circumference of the bone; defining a medial-lateral tilt line from a projected center point of the second set of points on the reference plane; and generating the anatomical coordinate system from first, second and third planes defined by the medial-lateral tilt line and vertical ridge line.

Another embodiment of the first aspect includes defining medial and lateral center points of respective medial and lateral portions of the virtual bone model from the second set of points. The projected center point is defined by the medial and lateral center points.

In one embodiment of this first aspect, the bone is a patella. The first plane is a transverse plane. The second plane is a coronal plane.

A second aspect of the present invention is a method to define a resection plane corresponding to the patellar coordinate system and a predetermined thickness of the implant. The radius of the implant on the resection plane is determined based on preset tolerance requirements with reference to the resection plane.

One embodiment of this second aspect is a method of determining a position of a resection cut on a bone, comprising generating an anatomical coordinate system coincident to a medial-lateral tilt of the bone; calculating a thickness of the bone, and defining a resection plane at a predetermined bone thickness and parallel to a medial-lateral tilt plane of the anatomical coordinate system.

In one embodiment of this first aspect, the bone is a patella. The first plane is a transverse plane. The second plane is a coronal plane.

In another embodiment, the bone thickness is defined as the distance between a most posterior and a most anterior point of the bone projected on a reference plane of the anatomical coordinate system. The reference plane is one of a transverse plane and a sagittal plane.

In yet another embodiment, the predetermined bone thickness is equal to one-third of the thickness of the bone.

In still yet another embodiment, the resection plane is cut using a navigated patella clamp having a tracker and a stylus.

In still yet another embodiment, the method further includes selecting a plurality of points on the periphery of the resection plane and defining a best fit circle therefrom such that the radial distance from a center of the circle to the periphery along the resection plane is substantially the same as the radius of the circle; and selecting a bone implant with a bone contacting surface having a radius equal to the radius of the circle.

In still yet another embodiment, the implant is located on the resection plane of the bone by positioning a center of the bone contacting surface of the implant to coincide with the center of the resection plane.

In still yet another embodiment, the implant is located by a navigated patella clamp having a tracker and a stylus.

A third aspect of the present invention is a method of utilizing a navigated patella clamp with a tracker and stylus to intraoperatively resect the patella and locate the implant according to the preoperative plan.

One embodiment of this third aspect is a method of generating an anatomical coordinate system for a virtual bone model of an irregularly shaped bone, comprising selecting a first set of points along a vertical ridge of the virtual bone model defining a vertical ridge line; creating a reference plane transverse to the vertical ridge line; selecting a second set of points about a circumference of the bone; defining a medial-lateral tilt line from a projected center point of the second set of points on the reference plane; and creating a first plane through the medial-lateral tilt line and parallel to the vertical ridge line, a second plane through the vertical ridge line and transverse to the first plane, and a third plane transverse to the first and second planes, wherein the first, second and third planes define the anatomical coordinate system.

One embodiment of this third aspect further comprises defining medial and lateral center points of respective medial and lateral portions of the virtual bone model from the second set of points.

In one embodiment, the projected center point is defined by the medial and lateral center points.

In another embodiment, the bone is a patella and the first plane is a transverse plane and the second plane is a coronal plane.

BRIEF DESCRIPTION OF THE DRAWINGS

A more complete appreciation of the subject matter of the present invention and the various advantages thereof can be realized by reference to the following detailed descriptions, in which reference is made to the accompanying drawings:

FIGS. 6A and 6B show perspective views of a patella with facet registration points and planes corresponding to the patellar coordinate system of the present invention;

FIG. 7 shows a side elevation view of a patella in a medial to lateral direction depicting a most posterior point on a ridge;

FIG. 11 is a schematic block diagram showing preoperative and intraoperative steps for a patella implant procedure of the present invention.

DETAILED DESCRIPTION

In describing preferred embodiments of the disclosure, reference will be made to directional nomenclature used in describing the human body. It is noted that this nomenclature is used only for convenience and that it is not intended to be limiting with respect to the scope of the invention.

As used herein, when referring to bones or other parts of the body, the term "anterior" means toward the front part or the face and the term "posterior" means toward the back of the body. The term "medial" means toward the midline of the body and the term "lateral" means away from the midline of the body. The term "superior" means closer to the heart and the term "inferior" means more distant from the heart.

Figure 1:
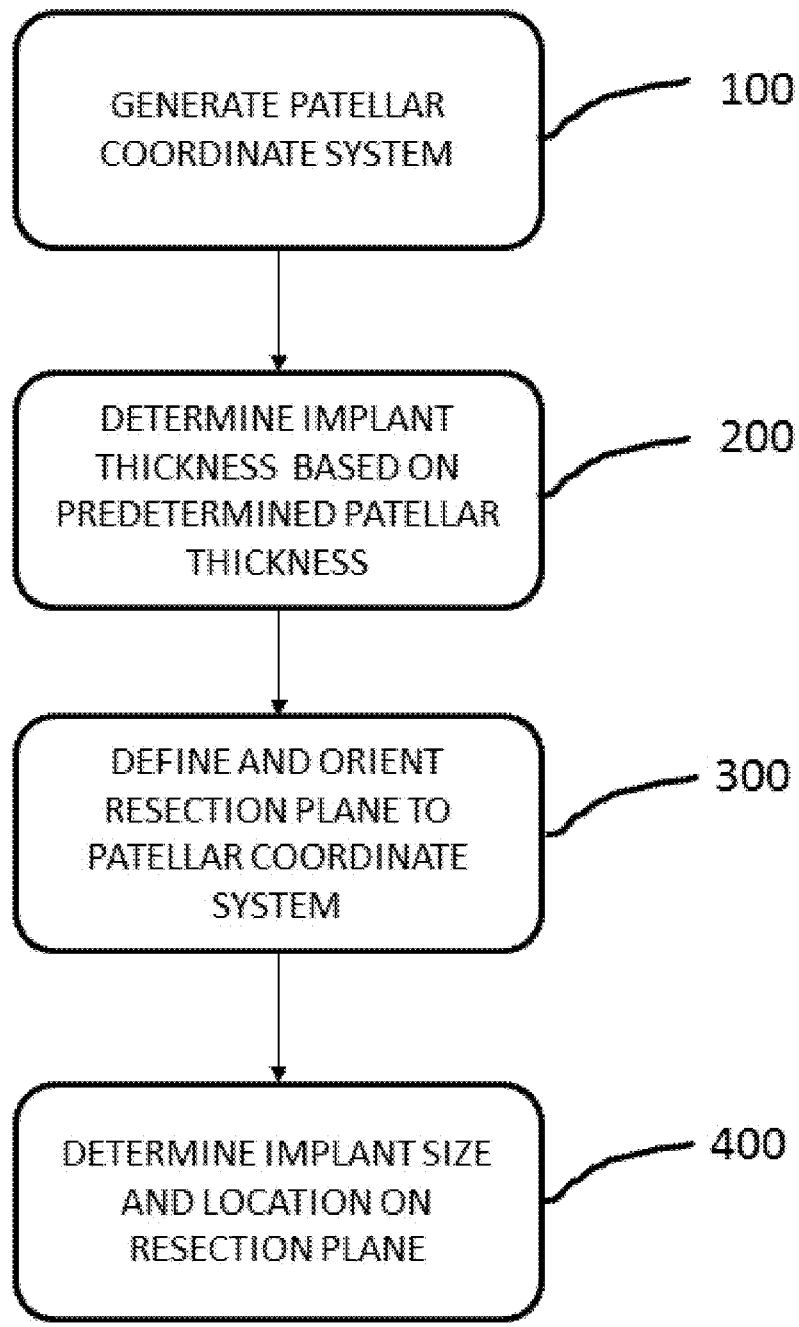
FIG. 1 is a flow chart describing steps for a preoperative patella planning procedure according to an embodiment of the present invention.

Referring to FIG. 1, there is shown a flow chart of the preoperative planning procedure steps for determining an implant size and location on a resection plane. The steps include: generating a patellar coordinate system 100, determining the implant thickness 200, defining and orienting the resection plane to coordinate with the patella coordinate system 300, and subsequently determining an implant radius and location on the resection plane 400. Steps shown in FIG. 1 may be performed preoperatively, and therefore allow a surgeon to determine the patella resection plane, patella implant size and position prior to surgery.

Figure 2:
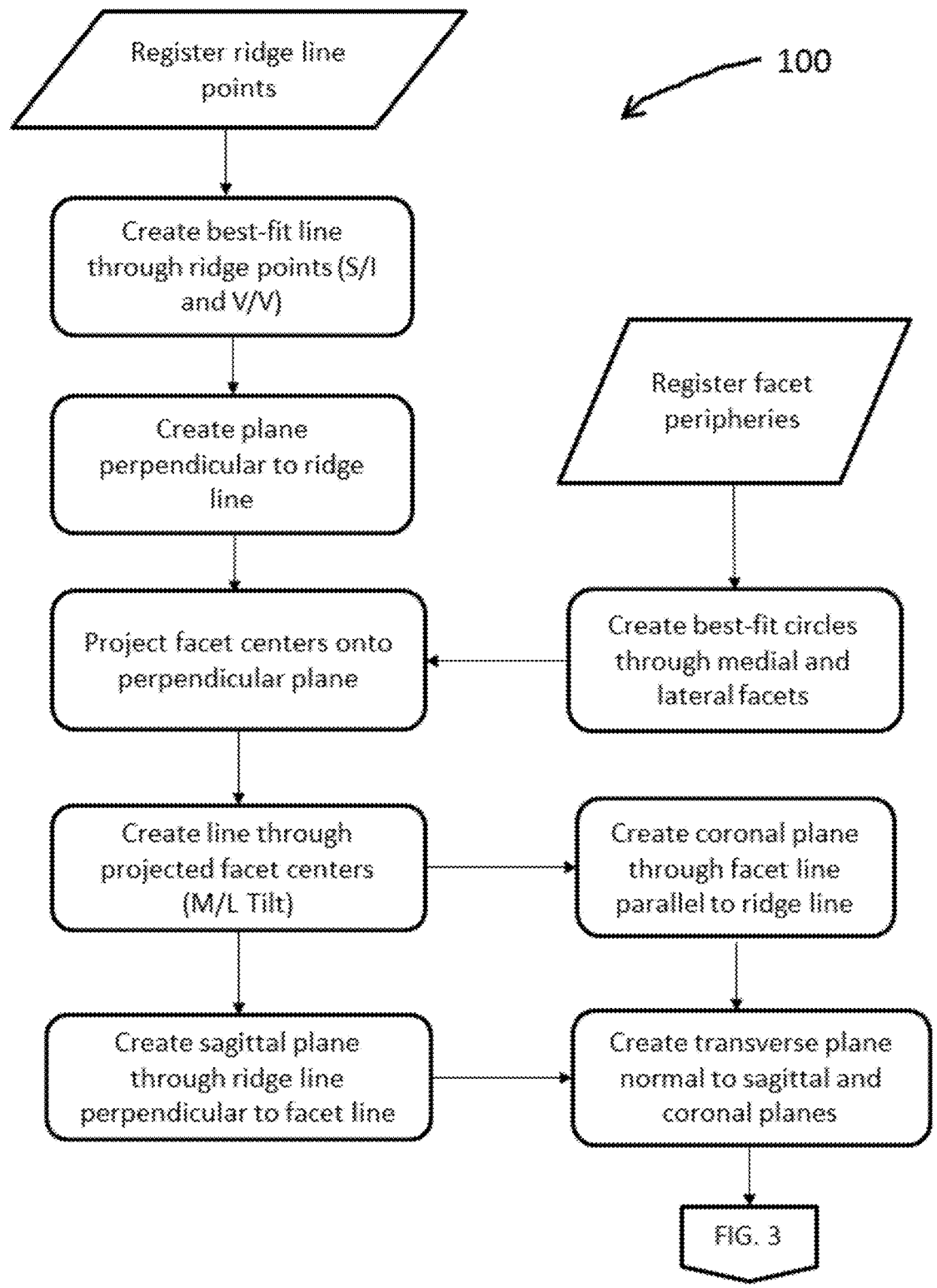
FIG. 2 is a flow chart describing steps to generate a patellar coordinate system according to the preoperative patella planning procedure of FIG. 1.

FIG. 2 shows a flow chart describing steps to generate a patellar coordinate system. A three-dimensional model of an unresected patella 102 projected on a graphic user interface is used to select vertical ridge points 106 on the posterior side of the patella as best shown in FIG. 6A. A ridge line 116 running in a superior to inferior direction is created by a best fit line connecting vertical ridge points 106 as best shown in FIG. 6B. A plane 108 perpendicular to the best fit line through ridge points is created thereafter. Peripheral points on a medial facet 110 and a lateral facet 112 of patella 102 are then selected and used to create best fit circles for the medial facet and lateral facet as shown in FIG. 6A. Best fit circle centers are then projected on plane 108 along the best fit ridge line. A facet line 114 is created by joining the projected centers. Facet line 114 represents the natural medial-lateral tilt of patella 102.

A coronal plane 118 through facet line 114 and parallel to ridge line 116, and a sagittal plane 130 through ridge line 116 and perpendicular to facet line 114 are then created. Patellar coordinate system 100 is completed by creating a transverse plane (not shown) normal to sagittal plane 130 and coronal plan 118. Patellar coordinate system 100 is aligned with the natural medial-lateral tilt of patella 102 representing the unique morphology of the patella.

Figure 3:
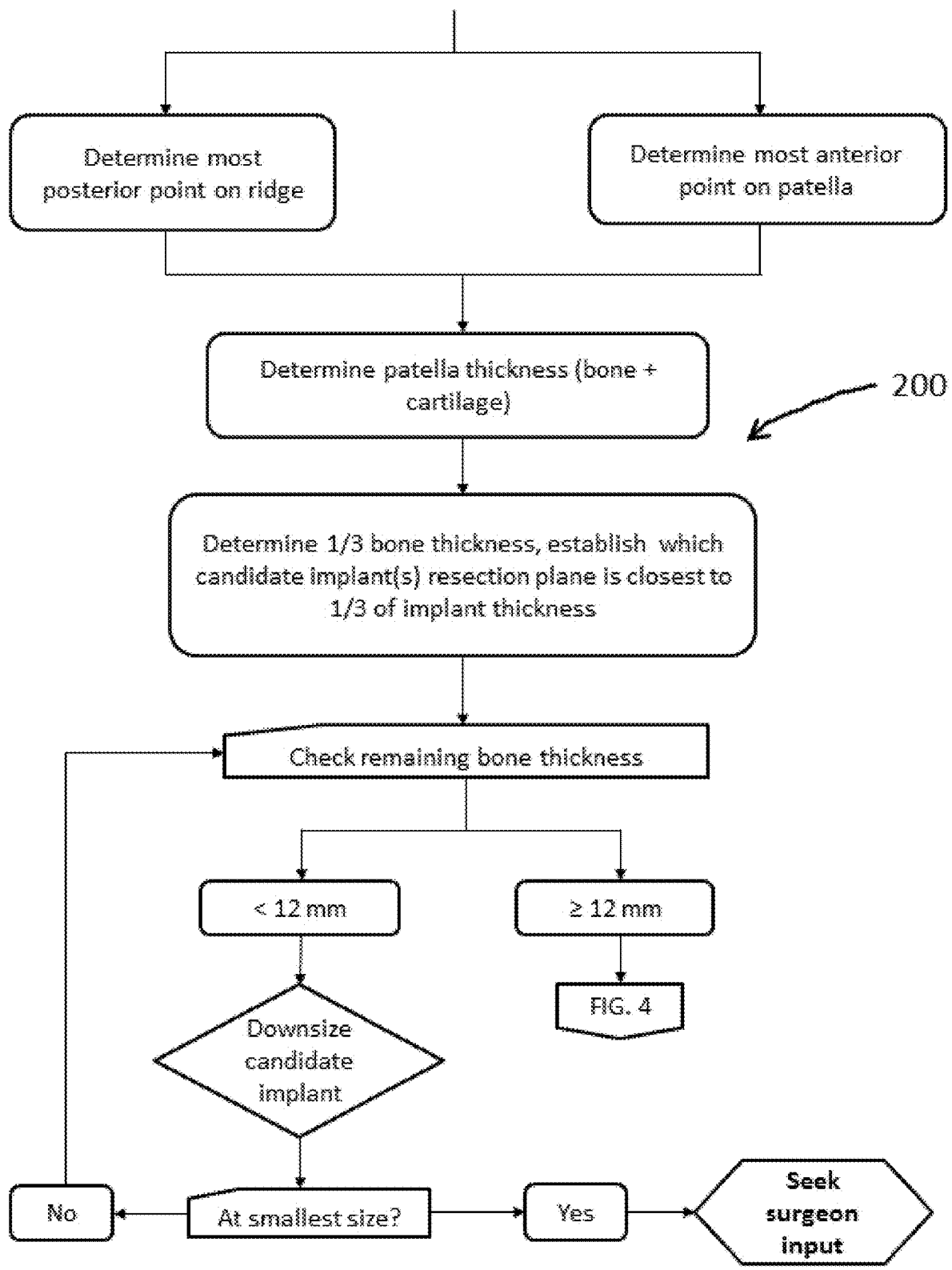
FIG. 3 is a flow chart describing steps to determine an implant thickness in reference to the patellar coordinate system of FIG. 2.
Figure 9:
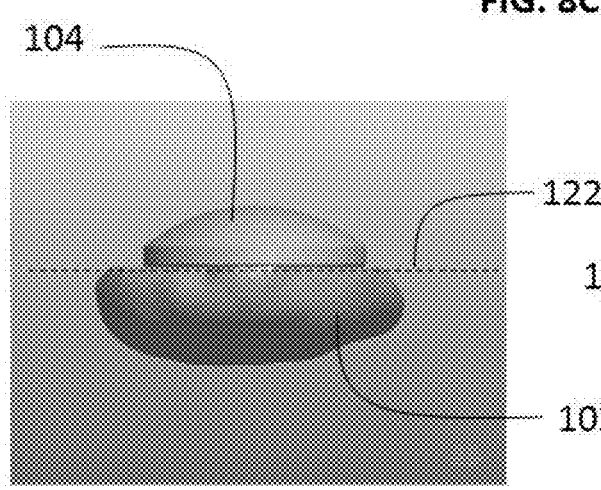
FIG. 9 shows a side elevation view in a medial to lateral direction of a patella with an implant according to the present invention.
Figure 10:
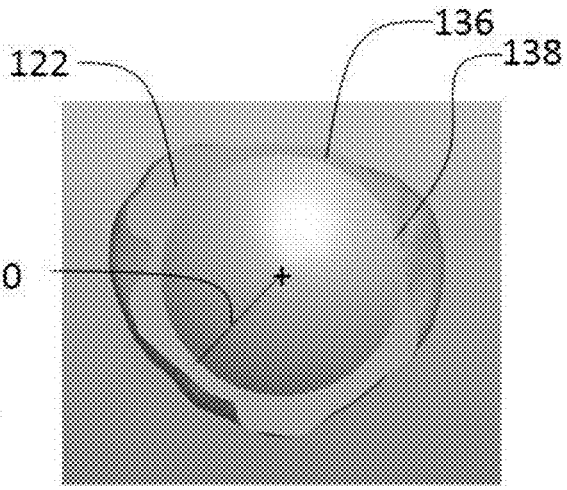
FIG. 10 shows a top view in a posterior to anterior direction of the patella and the implant of FIG. 9.

Referring to FIG. 3, there is shown a flow chart describing the steps to determine implant thickness 200. Patella 102 is aligned with the patellar coordinate system 100 as best shown in FIG. 7. A most posterior point 120 on the vertical ridge and a most anterior point (not shown) on the anterior surface of patella 120 are then determined. Thickness of patella 102 is defined by the distance between these two points projected on sagittal plane 130. One-third of this thickness will define the thickness of implant 104 as shown in FIG. 9. Thickness of implant 104 is equal to the resected bone, and therefore ensures that the combined resected patella with the implant has the same thickness as the unresected patella. To ensure that the resected patella is not subjected to excessive strains, a minimum patella thickness of 12 mm after resection must be maintained. If the resected bone thickness is less than 12 mm, the implant selection is downsized to reduce the bone resection thickness.

Figure 4:
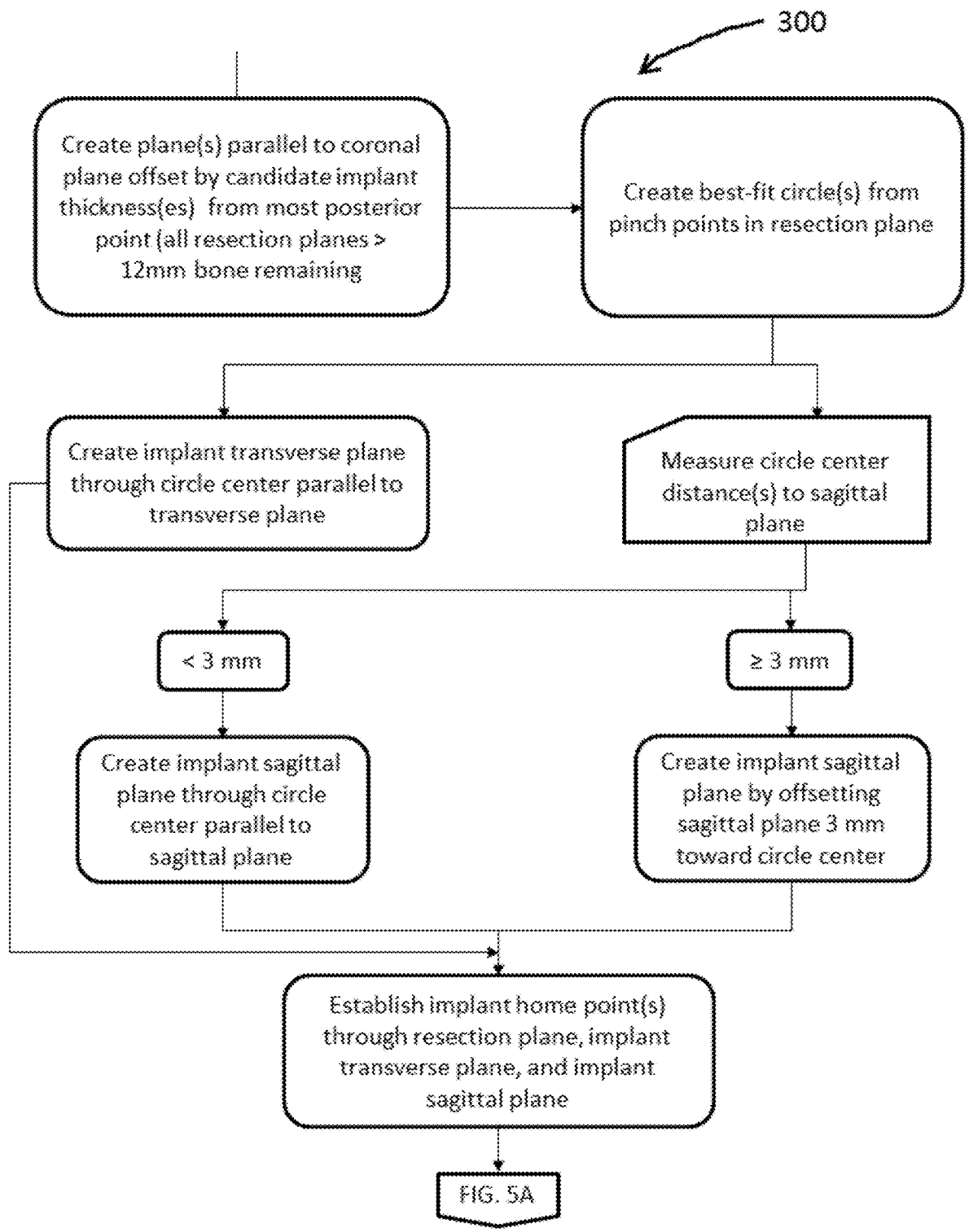
FIG. 4 is a flow chart describing steps to define and orient a resection plane based on the implant thickness of FIG. 3.
Figure 8A:
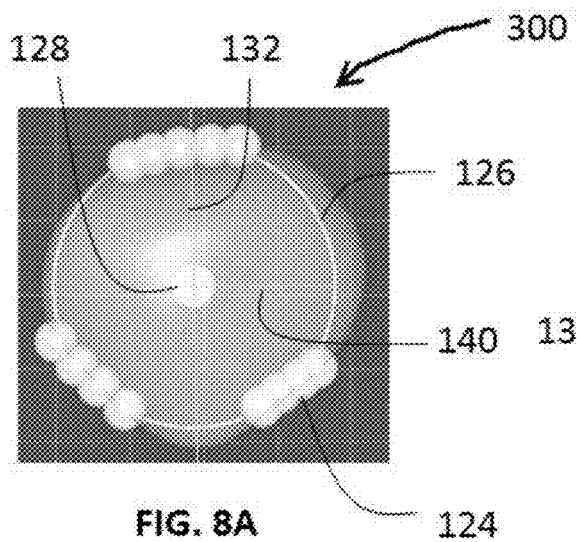
FIGS. 8A-C show top views of the patella in a posterior to anterior direction depicting the steps to determine implant radius and position.

FIG. 4 describes steps 300 to define and orient a resection plane 122 (shown in FIG. 9) with patellar coordinate system 100. Resection plane 122 is created parallel to coronal plane 118 at a distance equal to the thickness of implant 104 measured from most posterior point 120 on the vertical ridge. A best fit circle 126 with a center 128 is created through the peripheral pinch points 124 on resection plane 122 as shown in FIG. 8A. An implant transverse plane parallel to the patella transverse plane and running through center 128 is created (not shown). The distance between center 128 of the best fit circle and sagittal plane 130 is then measured along the implant transverse plane. If this distance is less than 3 mm, a sagittal plane 132 parallel to sagittal plane 130 and passing through center 128 is created. If, however, this distance is equal to or greater than 3 mm, offset sagittal plane 130 by a distance of 3 mm toward center 128 along the implant transverse plane. Implant home point 134 is now defined based on resection plane 122, sagittal plane 132 and center 128.

Figure 5A:
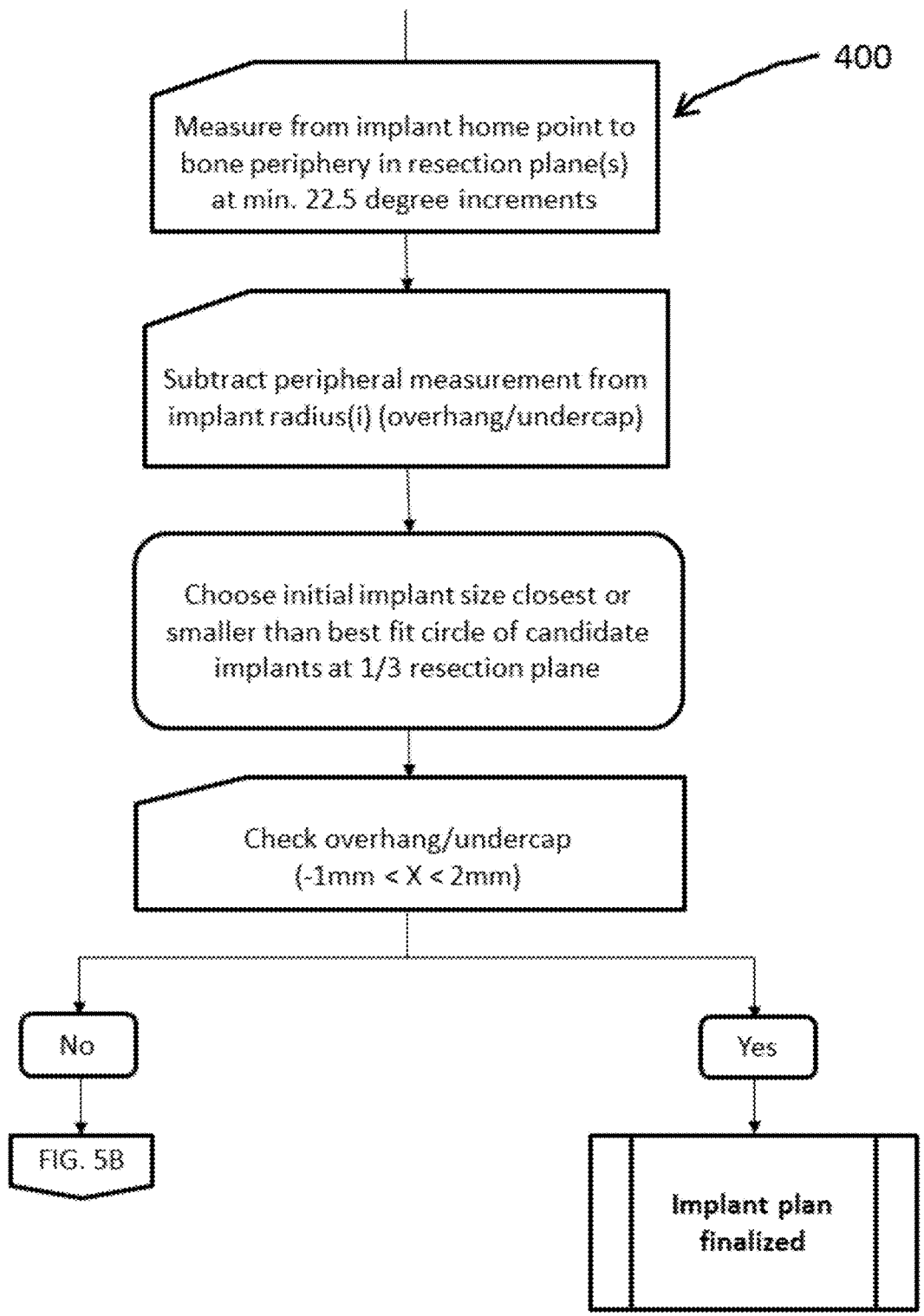
FIGS. 5A and 5B is a flow chart describing steps to determine an implant radius and location on the resection plane of FIG. 4.
Figure 8B:
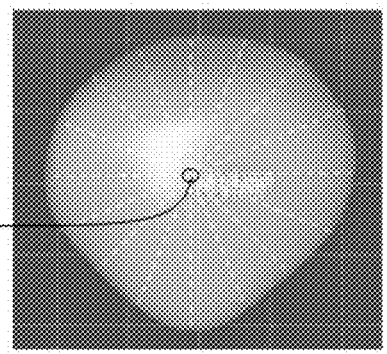
Figure 8C:
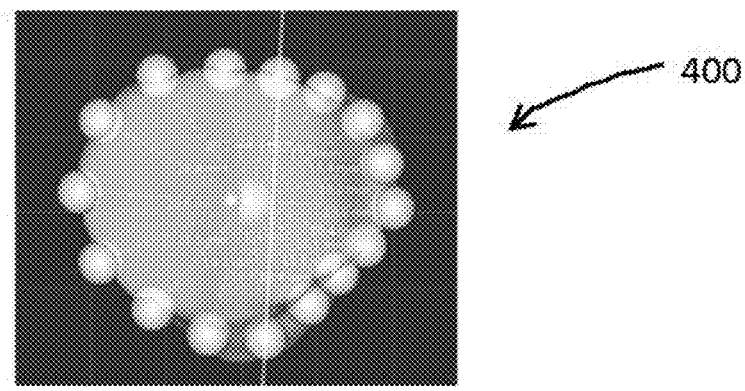

Referring now to FIG. 5A, there is shown a flow chart describing steps to size implant radius and locate implant 104 on resection plane 122. Multiple peripheral measurements from implant home point 134 to resection plane periphery at a maximum of 22.5 degree increments are taken as best shown in FIGS. 8B and 8C. An implant radius 140 matching a best fit circle of peripheral points on the resection plane is then selected. The difference between a peripheral measurement and the radius of the implant indicates overhang 138 or undercap 136. Overhang 138 occurs when the radius of the implant is larger than the peripheral measurement, and undercap 136 occurs when the radius of the implant is smaller than peripheral measurement. If the overhang is less than 1 mm and the undercap is less than 2 mm, the selected implant satisfies the required tolerance and is sized properly, thereby successfully completing the patella planning procedure.

Figure 5B:
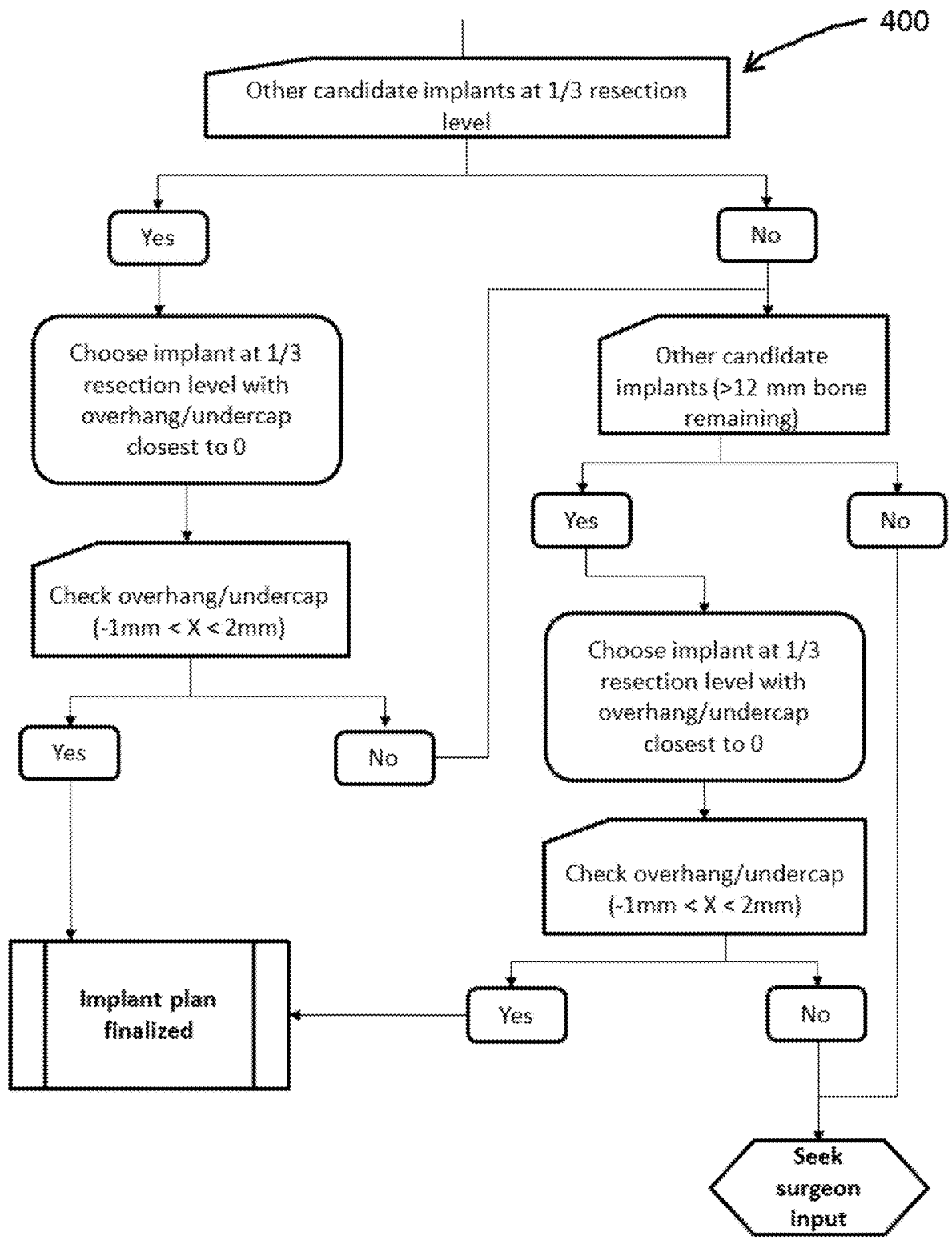

FIG. 5B describes additional steps that may be performed if the overhang and undercap tolerance are not satisfied by steps indicated in flow chart of FIG. 5A. Another implant, if available, having the same thickness, i.e., thickness equal to the resected patella, with a different radius that reduces overhang and undercap to the required tolerance is selected. If, however, there are no other suitable implants available, i.e., implants having the same thickness as the resected patella and radius of implant satisfying tolerance requirements, a new implant with a different thickness may be selected. However, resection plane location with new implant must ensure that at least 12 mm of patella bone is retained. Steps described in flow chart 300 (FIG. 4) and flow chart 400 (FIG. 5) can subsequently be performed to complete the planning procedure. While a minimum patella thickness of 12 mm is required according to the present embodiment, other embodiments may vary the minimum patella thickness requirement. Similarly, tolerance limits of the overhang and undercap of the implant specified in the present embodiment may be varied in other embodiments.

Referring now to FIG. 11, there is shown a schematic drawing of a block diagram outlining a preoperative plan and intraoperative steps required to complete a surgical method for a patella implant procedure according to another embodiment of the present invention. The preoperative plan consists of determining a patella resection plane (100, 200), implant selection and determining implant placement location (300, 400) as more fully explained above. Intraoperative steps include utilizing a device to enable the patella to be engaged in a planned position and orientation to carry out the resection and placement of the implant. A navigated patella clamp with a tracker may be used to intraoperatively inform the surgeon where to place the clamp on the patella (500) in the manner disclosed in U.S. patent application Ser. No. 15/087,202, the disclosure of which is hereby incorporated by reference herein. While the methods of the present invention disclosed as above set forth have been described in terms of a patella, it is to be understood that the term bone should be broadly construed to include other bone elements.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention.

The invention claimed is:

1. A method of generating an anatomical coordinate system for a virtual bone model of an irregularly shaped bone, comprising:
    displaying the virtual bone model of the bone on a graphical user interface;
    selecting a first set of points using the graphical user interface on a vertical ridge of the virtual bone model defining a vertical ridge line;
    creating a reference plane transverse to the vertical ridge line;
    selecting a second set of points using the graphical user interface about a circumference of the virtual bone model;
    defining a medial-lateral tilt line from a projected center point of the second set of points on the reference plane; and
    generating the anatomical coordinate system from first, second and third planes defined by the medial-lateral tilt line and vertical ridge line.

2. The method of claim 1, further comprising defining medial and lateral center points of respective medial and lateral portions of the virtual bone model from the second set of points.

3. The method of claim 2, wherein the projected center point is defined by the medial and lateral center points.

4. The method of claim 1, wherein the bone is a patella.

5. The method of claim 1, wherein the first plane is a transverse plane.

6. The method of claim 1, wherein the second plane is a coronal plane.

7. A method of determining a position of a resection cut on a bone, comprising:
    displaying a virtual bone model of the bone on a graphical user interface;
    creating a reference plane transverse to a vertical ridge line by selecting a first set of points using the graphical user interface on a vertical ridge of the virtual bone model to define the vertical ridge line;
    selecting a second set of points using the graphical user interface about a circumference of the virtual bone model;
    defining a medial-lateral tilt line from a projected center point of the second set of points on the reference plane;
    creating a medial-lateral tilt plane from the medial lateral line; generating an anatomical coordinate system coincident to the medial-lateral tilt of the bone;
    calculating a thickness of the bone; and
    defining a resection plane at a predetermined bone thickness and parallel to the medial-lateral tilt plane of the anatomical coordinate system.

8. The method of claim 7, wherein the bone is a patella.

9. The method of claim 7, wherein the bone thickness is defined as the distance between a most posterior and a most anterior point of the bone projected on a reference plane of the anatomical coordinate system.

10. The method of claim 9, wherein the reference plane is one of a transverse plane and a sagittal plane.

11. The method of claim 7, wherein the predetermined bone thickness is equal to one-third of the thickness of the bone.

12. The method of claim 7, wherein the resection plane is cut using a navigated patella clamp having a tracker and a stylus.

13. The method of claim 7, further comprising:
selecting a plurality of points on the periphery of the resection plane and defining a best fit circle therefrom such that the radial distance from a center of the circle to the periphery along the resection plane is substantially the same as the radius of the circle, and
selecting a bone implant with a bone contacting surface having a radius equal to the radius of the circle.

14. The method of claim 13, wherein the implant is located on the resection plane of the bone by positioning a center of the bone contacting surface of the implant to coincide with the center of the resection plane.

15. The method of claim 14, wherein the implant is located by a navigated patella clamp having a tracker and a stylus.

16. A method of generating an anatomical coordinate system for a virtual bone model of an irregularly shaped bone, comprising:
displaying the virtual bone model of the bone on a graphical user interface;
selecting a first set of points using the graphical user interface on a vertical ridge of the virtual bone model defining a vertical ridge line;
creating a reference plane transverse to the vertical ridge line;
selecting a second set of points using the graphical user interface about a circumference of the virtual bone model;
defining a medial-lateral tilt line from a projected center point of the second set of points on the reference plane; and
creating a first plane through the medial-lateral tilt line and parallel to the vertical ridge line, a second plane through the vertical ridge line and transverse to the first plane, and a third plane transverse to the first and second planes,
wherein the first, second and third planes define the anatomical coordinate system.

17. The method of claim 16, further comprising defining medial and lateral center points of respective medial and lateral portions of the virtual bone model from the second set of points.

18. The method of claim 17, wherein the projected center point is defined by the medial and lateral center points.

19. The method of claim 16, wherein the bone is a patella.

20. The method of claim 16, wherein the first plane is a transverse plane and the second plane is a coronal plane.

* * * * *